United States Patent
Lv et al.

(10) Patent No.: US 10,960,044 B2
(45) Date of Patent: Mar. 30, 2021

(54) POWDER FORMULATION HAVING HYPOGLYCEMIC AND HYPOLIPIDEMIC FUNCTIONS AND METHOD FOR PREPARING THE SAME

(71) Applicant: INFINITUS (CHINA) COMPANY LTD., Guangdong (CN)

(72) Inventors: Fang Lv, Guangdong (CN); Hongwei Zhao, Guangdong (CN); Qingtao Tang, Guangdong (CN)

(73) Assignee: INFINITUS (CHINA) COMPANY LTD., Guangdong (CN)

( * ) Notice: Subject to any disclaimer, the term of this patent is extended or adjusted under 35 U.S.C. 154(b) by 103 days.

(21) Appl. No.: 16/030,462

(22) Filed: Jul. 9, 2018

(65) Prior Publication Data
US 2019/0060391 A1   Feb. 28, 2019

(30) Foreign Application Priority Data
Aug. 24, 2017   (CN) .......................... 201710736702.X

(51) Int. Cl.
| | | |
|---|---|---|
| *A61K 36/28* | (2006.01) | |
| *A61K 36/00* | (2006.01) | |
| *A61K 36/8984* | (2006.01) | |
| *A61K 36/537* | (2006.01) | |
| *A61K 9/16* | (2006.01) | |
| *A61P 3/08* | (2006.01) | |
| *A61P 3/06* | (2006.01) | |
| *A23L 33/105* | (2016.01) | |
| *A23L 33/21* | (2016.01) | |
| *A61K 36/481* | (2006.01) | |
| *A61K 31/733* | (2006.01) | |
| *A61K 36/52* | (2006.01) | |
| *A61K 36/185* | (2006.01) | |
| *A61K 36/8945* | (2006.01) | |

(52) U.S. Cl.
CPC ........ *A61K 36/8984* (2013.01); *A23L 33/105* (2016.08); *A23L 33/21* (2016.08); *A61K 9/16* (2013.01); *A61K 9/1688* (2013.01); *A61K 31/733* (2013.01); *A61K 36/185* (2013.01); *A61K 36/481* (2013.01); *A61K 36/52* (2013.01); *A61K 36/537* (2013.01); *A61K 36/8945* (2013.01); *A61P 3/06* (2018.01); *A61P 3/08* (2018.01); *A23V 2002/00* (2013.01); *A61K 2236/00* (2013.01); *A61K 2236/331* (2013.01)

(58) Field of Classification Search
None
See application file for complete search history.

(56) References Cited

U.S. PATENT DOCUMENTS

| 2008/0102137 A1 | 5/2008 | Guffey | |
|---|---|---|---|
| 2014/0080906 A1* | 3/2014 | Ervin | A23C 9/137 |
| | | | 514/547 |

FOREIGN PATENT DOCUMENTS

| CN | 101371902 A | * | 2/2009 |
|---|---|---|---|
| CN | 101579463 A | * | 11/2009 |
| CN | 101843763 A | * | 9/2010 |
| CN | 104705443 A | * | 6/2015 |
| CN | 105596458 A | * | 5/2016 |
| CN | 106177480 A | | 12/2016 |
| WO | 2008054695 A2 | | 5/2008 |

OTHER PUBLICATIONS

Guo Lizhong, Analysis of Pharmacological Evaluation of Compound Dendrobium Mixture in the Treatment of Type 2 Diabetes Mellitus, China Health Standard Management, vol. 6, No. 21,2015,The Affiliated Hospital to Changchun University of Chinese Medicine, Changchun 130021, China.
Li jun, An observation on the treatment of diabetes with the combination of Astragalus, Rehmannia Root, Salvia miltiorrhiza,Seek Medical and Ask the Medicine, vol. 10, No. 2, 2012,Liyuan hospital of Tongzhou District of Beijing, Beijing 101100 ,China.
Lu Zhenhua, Effects of Cyclocarya paliurus Leaves on Blood Glucose, Blood Lipid and Antioxidation in Diabetic Rats, Journal of Hubei University of Chinese Medicine,Feb. 2017, vol. 19, No. 1, Clinical Laboratory,Hubei Provincial Hospital of Chinese Medicine, Wuhan 430061.
Hang Yue-Yu,Pharmacological experiments on lowing the blood sugar and blood Lipids level of Rhizoma Dioscoreae, Journal of Plant Resources and Environment, 1994, 3(4) : 59~60, Institute of Botany, Jiangsu Province and Academia Sinica, Nanjing 210014.
Zeng Xiao-yu,Recent advance and future trend of Inulin research and development,China Food Additives,Food and Bioengineering College, Henan University of Science and Technology, Luoyang 471003,Aug. 15, 2010 pp. 224-225.

(Continued)

*Primary Examiner* — Michael Barker
*Assistant Examiner* — Randall O Winston
(74) *Attorney, Agent, or Firm* — Yue (Robert) Xu; Apex Attorneys at Law, LLP

(57) ABSTRACT

The present disclosure relates to the field of health care products, disclosing a powder made from inulin, FOLIUM *CYCLOCARYA PALIURUS*, RHIZOMA *DIOSCOREA* OPPOSITE, RADIX *ASTRAGALUS* MEMBRANACEUS, CAULIS *DENDROBIUM* and RADIX ET RHIZOMA *SALVIA* MILTIORRHIZA. The raw materials of the powder are all from natural Chinese herbal medicine without addition of excipient. In addition, dosage required for the powder is small; it can be directly dissolved in water for taking; it is soluble in cold water and can be absorbed quickly. The method for preparing the powder in the present disclosure is simple and suitable for large-scale production. Also, it is easy to be carried. The powder obtained has a good stability and long storage time. Experiments show that the powder of the present disclosure has greatly hypoglycemic and hypolipidemic effects, therefore can be used to prepare the health care foods having hypoglycemic and hypolipidemic effect.

5 Claims, No Drawings

(56) References Cited

OTHER PUBLICATIONS

Zhenyong Dong, Medication for diabetes,Rational Use of Endocrine Systems, pp. 293-295, China Pharmaceutical Sciences Press, 1st Edition, Jan. 31, 2009.
Xie Xin-cai et al., Diabetes (wasting-thirst), Clinical Chinese Medicine, p. 447, China Publishing House of Traditional Chinese Medicine, 1st edition, Jan. 31, 2017.
The 2nd Office Action regarding Chinese Patent Application No. CN201710736702.X, dated Sep. 30, 2020. English Translation Provided by http://globaldossier.uspto.gov.
Wenbin He, Diabetes, Shanxi Science and Technology Publishing, the 1st Edition, Jun. 30, 2015, pp. 61-63.
Dalu Zhang, Scientific Interpretation of Health Food: Choosing to Eat Well to Protect Health, China Science and Technology Publishing House of Traditional Chinese Medicine, The 1st edition, Jan. 31, 2016, p. 92.
The 1st Office Action regarding Chinese Patent Application No. CN201710736702.X, dated Mar. 19, 2020. English Translation Provided by http://globaldossier.uspto.gov.

* cited by examiner

POWDER FORMULATION HAVING HYPOGLYCEMIC AND HYPOLIPIDEMIC FUNCTIONS AND METHOD FOR PREPARING THE SAME

CROSS REFERENCE TO RELATED APPLICATIONS

This application claims the priority of Chinese Patent Application No. 201710736702.X, filed on Aug. 24, 2017, and titled with "POWDER FORMULATION HAVING HYPOGLYCEMIC AND HYPOLIPIDEMIC FUNCTIONS AND METHOD FOR PREPARING THE SAME", and the disclosures of which are hereby incorporated by reference.

FIELD

The present disclosure relates to the field of health care products, specifically to a powder formulation, a method for preparing the same and use thereof, and more specifically to a powder formulation mainly made from natural Chinese herbal medicine and having hypoglycemic and hypolipidemic functions and the method for preparing the same.

BACKGROUND

Hyperglycemia and hyperlipidemia are "rich people's diseases" derived from modern life, and they exist either alone or linked to each other. Hyperlipidemia and hyperglycemia are sources of many diseases. Hyperglycemia causes lesions in various tissues and organs of the body, resulting in the occurrence of acute and chronic complications, for example, pancreatic failure, dehydration, electrolyte imbalance, nutritional deficiency, decreased resistance, impaired renal function, neuropathy, fundus diseases, diabetes and so on. Hyperlipidemia is a risk factor of stroke, coronary heart disease, myocardial infarction, and sudden death. In addition, hyperlipidemia is also an important risk factor for promoting abnormal glucose tolerance and diabetes. Hyperlipidemia also leads to fatty liver, liver cirrhosis, cholelithiasis, pancreatitis, retinal hemorrhage, blindness, peripheral vascular disease, claudication and hyperuricemia.

People's living standard has increased significantly in recent years, and consumption concept and health concept of people have changed a lot. In order to avoid the adverse effects of being unhealthy, people pay more and more attention to the use of nutraceuticals. Currently, most of the health care foods for improving hypertension, hyperglycemia and hyperlipidemia are in the form of oral liquid. Oral liquid has disadvantages of inconvenience of carrying, poor stability and short storage time. Large doses of adjuvants such as starch and hydroxymethyl cellulose are often added to the tablet when the tablets are made, which causes a long disintegration time. At the same time, it is inconvenient for people who have dysphagia, such as old people and children.

SUMMARY

In view of this, in order to overcome the deficiencies in the prior art, an object of the present disclosure is providing a powder formulation, a method for preparing the same and use thereof. In the present disclosure, the powder formulation having hypoglycemic and hypolipidemic functions is mainly made from natural Chinese herbal medicine, therefore the powder has natural components and without addition of excipients.

In order to achieve the goal of the present disclosure, the following technical solutions are used in the present disclosure.

A powder formulation is made from inulin, FOLIUM *CYCLOCARYA PALIURUS*, RHIZOMA *DIOSCOREA* OPPOSITE, RADIX *ASTRAGALUS* MEMBRANACEUS, CAULIS *DENDROBIUM* and RADIX ET RHIZOMA *SALVIA* MILTIORRHIZA as starting materials.

Therein, preferably, the mass ratio of inulin, FOLIUM *CYCLOCARYA PALIURUS*, RHIZOMA *DIOSCOREA* OPPOSITE, RADIX *ASTRAGALUS* MEMBRANACEUS, CAULIS *DENDROBIUM* and RADIX ET RHIZOMA *SALVIA* MILTIORRHIZA is (0.5~3):(4~8):(0.5~3):(0.5~3):(0.1~2):(0.1~2).

In some embodiments, the mass ratio of inulin, FOLIUM *CYCLOCARYA PALIURUS*, RHIZOMA *DIOSCOREA* OPPOSITE, RADIX *ASTRAGALUS* MEMBRANACEUS, CAULIS *DENDROBIUM* and RADIX ET RHIZOMA *SALVIA* MILTIORRHIZA is 1.5:8:1:1:0.4:0.1.

In some embodiments, the mass ratio of inulin, FOLIUM *CYCLOCARYA PALIURUS*, RHIZOMA *DIOSCOREA* OPPOSITE, RADIX *ASTRAGALUS* MEMBRANACEUS, CAULIS *DENDROBIUM* and RADIX ET RHIZOMA *SALVIA* MILTIORRHIZA is 0.5:4:2:2:1:0.5.

In some embodiments, the mass ratio of inulin, FOLIUM *CYCLOCARYA PALIURUS*, RHIZOMA *DIOSCOREA* OPPOSITE, RADIX *ASTRAGALUS* MEMBRANACEUS, CAULIS *DENDROBIUM* and RADIX ET RHIZOMA *SALVIA* MILTIORRHIZA is 1.2:6:1:1:0.5:0.5.

The present disclosure further provides a method for preparing the powder formulation, comprising:

1) adding water to FOLIUM *CYCLOCARYA PALIURUS* for extraction, and collecting the extract upon filtration;

2) mixing RHIZOMA *DIOSCOREA* OPPOSITE, RADIX *ASTRAGALUS* MEMBRANACEUS, CAULIS *DENDROBIUM* and RADIX ET RHIZOMA *SALVIA* MILTIORRHIZA, adding water to the mixture for extraction, and collecting the extract upon filtration;

3) respectively adding inulin to the extracts of step 1) and step 2), drying the extracts and mixing; or combing the extracts of step 1) and step 2), adding inulin to the extracts and drying;

4) pulverizing and sieving, or granulating and sieving after pulverizing;

and wherein, there is no special restriction to the order of step 1) and step 2).

The method for preparing the powder formulation in the present disclosure, wherein the extraction in step 1) is preferably selected from a group consisting of decoction extraction, low-temperature high-speed counter-current extraction and ultrasonic extraction.

Preferably, the decoction extraction is performed by adding water 12 to 25 times the weight of the starting materials and extracting for 40 to 60 minutes in a first extraction, and then adding water 10 to 13 times the weight of the starting materials and extracting for 10 to 40 minutes in a second extraction. In some embodiments, the decoction extraction is performed by adding water 20 times the weight of the starting materials and extracting for 2 hours in a first extraction, and then adding water 10 times the weight of the starting materials and extracting for 10 minutes in a second extraction.

Preferably, the low-temperature high-speed counter-current extraction is performed by adding water 12 to 25 times the weight of the starting materials at temperature between 40 and 60° C. and extracting for 40 to 60 minutes. In some embodiments, the low-temperature high-speed counter-current extraction is performed by adding water 25 times the weight of the starting materials at 60° C. and extracting for 1 hour.

Preferably, the ultrasonic extraction is performed by adding water 12 to 25 times the weight of the starting materials at temperature between 40 and 60° C. and extracting for 40 to 60 minutes, and the ultrasonic frequency is from 20 to 50 kHZ. In some embodiments, the ultrasonic extraction is performed by adding water 15 times the weight of the starting materials at 60° C. and extracting for 60 minutes, and the ultrasonic frequency is 50 kHZ.

In the method for preparing the powder formulation of the present disclosure, the extraction in step 2) is decoction extraction.

Further, the decoction extraction is preferably performed by adding water 8 to 15 times the weight of the starting materials and extracting for 40 minutes to 3 hours in a first extraction, and adding water 6 to 12 times the weight of the starting materials and extracting for 20 minutes to 2 hours in a second extraction.

In some embodiments, RHIZOMA DIOSCOREA OPPOSITE, RADIX ASTRAGALUS MEMBRANACEUS, CAULIS DENDROBIUM and RADIX ET RHIZOMA SALVIA MILTIORRHIZA are mixed and extracted by adding water, and the extraction is performed twice, wherein in the first extraction, water 12 times the weight of the starting materials is added and extraction is carried out for 2 hours, and in the second extraction, water 8 times the weight of the starting materials is added and extraction is carried out for 1 hour. In some embodiments, RHIZOMA DIOSCOREA OPPOSITE, RADIX ASTRAGALUS MEMBRANACEUS, CAULIS DENDROBIUM and RADIX ET RHIZOMA SALVIA MILTIORRHIZA are mixed and extracted by adding water, and the extraction is performed twice, wherein in the first extraction, water 15 times the weight of the starting materials is added and extraction is carried out for 40 minutes, and in the second extraction, water 6 times the weight of the starting materials is added and extraction is carried out for 2 hours. In other embodiments, RHIZOMA DIOSCOREA OPPOSITE, RADIX ASTRAGALUS MEMBRANACEUS, CAULIS DENDROBIUM and RADIX ET RHIZOMA SALVIA MILTIORRHIZA are mixed and extracted by adding water, and the extraction is performed twice, wherein in the first extraction, water 8 times the weight of the starting materials is added and extraction is carried out for 2 hours, and in the second extraction, water 12 times the weight of the starting materials is added and extraction is carried out for 20 minutes.

The method for preparing the powder formulation of the present disclosure further comprises a concentration step prior to adding inulin in step 3). That is, respectively concentrating the extracts of step 1) and step 2), adding inulin to them, drying and mixing, or combing the extracts of step 1) and step 2), concentrating, adding inulin and drying.

Preferably, the concentration is vacuum concentration or reverse osmosis concentration.

Further, the drying of step 3) is selected from the group consisting of spray drying, freeze drying, belt drying, microwave drying and vacuum drying.

Preferably, after drying in the method for preparing of the present disclosure, there are pulverization and sieving processes or granulation and sieving processes after pulverization. The particle size after pulverization is preferably controlled between 40 meshes and 80 meshes.

The present disclosure also provides use of the powder formulation in preparing health care food having hypoglycemic and hypolipidemic functions.

In view of the technical solutions above, the present disclosure provides a powder formulation made from inulin, FOLIUM CYCLOCARYA PALIURUS, RHIZOMA DIOSCOREA OPPOSITE, RADIX ASTRAGALUS MEMBRANACEUS, CAULIS DENDROBIUM and RADIX ET RHIZOMA SALVIA MILTIORRHIZA. The raw materials of the powder are all from natural Chinese herbal medicine without addition of excipient. It is clean and has natural components, in line with people's pursuit of natural and health foods. In addition, dosage required for the powder is small; it can be dissolved in water for taking; it is soluble in cold water and can be absorbed quickly. The method for preparing the powder in the present disclosure is simple and suitable for large-scale production. Also, it is easy to be carried. The powder obtained has a good stability and long storage time. Experiments show that the powder of the present disclosure has greatly hypoglycemic and hypolipidemic functions, therefore it can be used to prepare the health care foods having hypoglycemic and hypolipidemic functions.

DETAILED DESCRIPTION

The present disclosure provides a powder formulation having hypoglycemic and hypolipidemic functions, the method for preparing the same and the application thereof. One of ordinary skill in the art can learn from the contents herein and improve the process parameters appropriately. In particular, it shall be noted that all the similar substitutions and modifications are apparent to one of ordinary skill in the art and are to be considered within the scope of the present invention. The method and product of the present invention have been described with preferred examples. It is apparent that one of the ordinary skill in the art can make change or modify the combination to the method and product of the present invention without departing from the spirit, scope and spirit of the invention, therefore realizing and applying the techniques of the present invention.

In order to understand the present disclosure further, the technical solutions in the embodiments of the present disclosure will be described clearly and completely herein in conjunction with the examples of the present disclosure. Apparently, the described examples are only a part of the examples of the present disclosure, rather than all examples. Based on the examples in the present disclosure, all of other examples, made by one of ordinary skill in the art without any creative efforts, fall into the protection scope of the present disclosure.

Without special illustration, all the reagents in the examples of the present disclosure are commercial products, which can be purchased on the market.

Example 1

Powder Formulation of the Present Disclosure

Formulation

| | |
|---|---|
| Inulin | 150 mg |
| FOLIUM CYCLOCARYA PALIURUS | 800 mg |
| RHIZOMA DIOSCOREA OPPOSITE | 100 mg |
| RADIX ASTRAGALUS MEMBRANACEUS | 100 mg |
| CAULIS DENDROBIUM | 40 mg |
| RADIX ET RHIZOMA SALVIA MILTIORRHIZA | 10 mg |

Method for preparing: water which was 25 times the weight of FOLIUM *CYCLOCARYA PALIURUS* was added to the FOLIUM *CYCLOCARYA PALIURUS* and extraction was performed by low-temperature high-speed countercurrent extraction. The extraction temperature was 60° C. and the duration of the extraction was 1 hour. The extract was filtrated and vacuum concentrated. Water was added to RHIZOMA *DIOSCOREA* OPPOSITE, RADIX *ASTRAGALUS* MEMBRANACEUS, CAULIS *DENDROBIUM*, RADIX ET RHIZOMA *SALVIA* MILTIORRHIZA and decoction extraction was performed twice. At the first extraction, water which was 15 times the weight of the starting materials was added and the extraction was performed for 3 hours. At the second extraction, water which was 6 times the weight of the starting materials was added and the extraction was performed for 2 hours. The two extracts were combined and subjected to vacuum concentration. The concentrates were combined and subjected to spray drying. Inulin was added and the mixture was pulverized, giving the powder formulation.

Example 2

Powder Formulation of the Present Disclosure

Formulation:

| | |
|---|---|
| Inulin | 50 mg |
| FOLIUM *CYCLOCARYA PALIURUS* | 400 mg |
| *RHIZOMA DIOSCOREA* OPPOSITE | 200 mg |
| RADIX *ASTRAGALUS MEMBRANACEUS* | 200 mg |
| CAULIS *DENDROBIUM* | 100 mg |
| RADIX ET RHIZOMA *SALVIA MILTIORRHIZA* | 50 mg |

Method for preparing: water which was 15 times the weight of FOLIUM *CYCLOCARYA PALIURUS* was added to the FOLIUM *CYCLOCARYA PALIURUS* and extraction was performed by ultrasonic extraction at 50 kHZ and 60° C. for 60 minutes. The extract was filtrated and subjected to reverse osmosis concentration. Water was added to RHIZOMA *DIOSCOREA* OPPOSITE, RADIX *ASTRAGALUS* MEMBRANACEUS, CAULIS *DENDROBIUM*, RADIX ET RHIZOMA *SALVIA* MILTIORRHIZA and extracted for twice. At the first extraction, water which was 12 times the weight of the starting materials was added and the extraction was performed for 1 hour. At the second extraction, water which was 8 times the weight of the starting materials was added and the extraction was performed for 0.5 hour. The two extracts were combined and subjected to vacuum concentration. The concentrates were combined and subjected to belt drying. Inulin was added and the mixture was pulverized, giving the powder formulation.

Example 3

Powder Formulation of the Present Disclosure

Formulation:

| | |
|---|---|
| Inulin | 120 mg |
| FOLIUM *CYCLOCARYA PALIURUS* | 600 mg |
| RHIZOMA *DIOSCOREA OPPOSITE* | 100 mg |
| RADIX *ASTRAGALUS MEMBRANACEUS* | 100 mg |
| CAULIS *DENDROBIUM* | 50 mg |
| RADIX ET RHIZOMA *SALVIA MILTIORRHIZA* | 50 mg |

Method for preparing: FOLIUM *CYCLOCARYA PALIURUS* were subjected to decoction extraction. At the first extraction, water which was 20 times the weight of the FOLIUM *CYCLOCARYA PALIURUS* was added and extraction was performed for 1 hour. At the second extraction, water which was 10 times the weight of the FOLIUM *CYCLOCARYA PALIURUS* was added and extraction was performed for 10 minutes, followed by filtration. The two extracts were combined and subjected to reverse osmosis concentration and freeze drying. Water was added to RHIZOMA *DIOSCOREA* OPPOSITE, RADIX *ASTRAGALUS* MEMBRANACEUS, CAULIS *DENDROBIUM*, RADIX ET RHIZOMA *SALVIA* MILTIORRHIZA and extraction was performed for twice. At the first extraction, water which was 8 times the weight of the starting materials was added and the extraction was performed for 2 hours. At the second extraction, water which was 12 times the weight of the starting materials was added and the extraction was performed for 20 minutes. The two extracts were combined and subjected to vacuum concentration and spray drying. The resulting powder was mixed with the FOLIUM *CYCLOCARYA PALIURUS* freeze drying powder. Inulin was added and the mixture was pulverized, giving the powder formulation.

Experimental Example 1

Hypoglycemic Effect Test

1. Test Sample

The powder formulation sample prepared in Example 3 was used for the functional experiments.

2. Experimental Animal

| | |
|---|---|
| Animals | SD rat; ICR mouse |
| Sex/Group | 18 to 20♂/group; 15 to 20♂/group |
| Weight | 150 to 170 g; 22 to 25 g |

3. Grouping and Administration Schedule of the Test Sample

In the experiment, there were three dosing groups, one model group, one positive control group (metformin hydrochloride tablets), one blank group and one negative control group. The methods for preparing the samples were shown hereinafter.

Method for preparing the solution of the test sample (500 mg/kg): 2.3011 g of the test sample was precisely weighed and 46 mL of distilled water was added to prepare a solution of 0.05 g/mL, i.e., high-dose group of the test sample (500 mg/kg, 1 mL/100 g), which was equal to 30 times the recommended amount for human.

Method for preparing the solution of the test sample (170 mg/kg): 0.6970 g of the test sample was precisely weighed and 41 mL of distilled water was added to prepare a solution of 0.017 g/mL, i.e., medium-dose group of the test sample (170 mg/kg, 1 mL/100 g), which was equal to 10 times the recommended amount for human.

Method for preparing the solution of the test sample (85 mg/kg): 0.3396 g of the test sample was precisely weighed and 40 mL of distilled water was added to prepare a solution of 0.0085 g/mL, i.e., low-dose group of the test sample (85 mg/kg, 1 mL/100 g), which was equal to 5 times the recommended amount for human.

Method for preparing the negative control group (normal animal group): test sample solution (500 mg/kg): 2.3011 g of the test sample was precisely weighed and 46 mL of distilled water was added to prepare a solution of 0.05 g/mL, i.e., negative control group (500 mg/kg, 1 mL/100 g), which was equal to 30 times the recommended amount for human.

Method for preparing the positive control sample: the metformin hydrochloride tablet was milled into fine powders by a mortar, 0.1470 g powder was precisely weighed and transferred to a 10 mL-centrifugal tube. 5 mL of distilled water was added by a pipette to prepare a solution with a concentration of 0.023 g/mL, i.e., metformin positive control group for mouse (230 mg/kg, 0.1 ml/10 g), which was equal to 13.5 times the recommended amount for human.

The mice were weighed after 1-day adaptive feed, and the mice were weighed once a week and recorded.

The administration of test sample to the rats lasted for 45 days, and the administration to mice lasted for 55 days.

4. Effects of Test Sample on Lowering Blood Glucose in Mice 4.1 Test of Fasting Blood Glucose and Glucose Tolerance in Mice After 3-day of adaptive housing with normal feeding, 15 mice were randomly chosen and subjected to fasting for 3 to 5 hours. The fasting blood glucose value was measured as the basal blood glucose value of this batch of animals. Thereafter, the mice were subjected to fasting for 24 hours (with free access to water). Except for the blank group and the negative control group, 96 mg/kg of alloxan (fresh prepared) were injected via caudal vein to establish the model, at an administration amount of 0.1 mL/10 g. 4 days later, the animals were fasted for 3 to 5 hours and the blood glucose was tested. Animals with blood glucose of 10 to 25 mmol/L were considered as hyperglycemia model animals. The fasting blood glucose value of mice was tested every two week. After the experiments, animals in each group were fasted for 3 to 4 hours, and the fasting blood glucose, glucose tolerance, blood glucose decreasing rate and the area under the blood glucose curve were tested.

$$\text{Blood glucose decreasing rate \%} = \frac{\text{Blood glucose before the experiment} - \text{Blood glucose after the experiment}}{\text{Blood glucose before the experiment}} \times 100\%$$

$$\text{Area under the blood glucose curve} = \frac{(\text{Blood glucose at 0 hour} + \text{Blood glucose at the 0.5th hour}) \times 0.5}{2} + \frac{(\text{Blood glucose at the 2nd hour} + \text{Blood glucose at the 0.5th hour}) \times 1.5}{2}$$

4.2 Organ Coefficient

The mice were subjected to euthanasia and dissection. Hearts, livers, spleens, lungs, kidneys and pancreases of the mice were weighed, imaged and recorded, respectively. The organ coefficients were calculated. In addition, pancreases from each group were respectively immersed into formalin-containing bottles, and the sections were sent for pathological examination.

4.3 Experimental Results 4.3.1 Changes of Body Weight Growth Shown in Table 1

TABLE 1

| Group | Number of Animals | Dosage (mg/kg) | 1 d | 2 d | 6 d | 8 d | 11 d |
|---|---|---|---|---|---|---|---|
| Blank Group | 15 | — | 24.0 ± 2.7 | 27.1 ± 3.2 | 31.0 ± 1.2 | 32.7 ± 1.1 | 35.0 ± 1.9 |
| Negative control group | 18 | 510 | 23.1 ± 2.2 | 25.2 ± 2.3 | 31.4 ± 1.7 | 33.3 ± 2.0 | 33.5 ± 3.1 |
| Model Group | 18 | — | 20.8 ± 2.4 | 22.3 ± 2.8 | 21.2 ± 2.7## | 23.5 ± 2.9## | 24.6 ± 3.9## |
| Positive control group | 20 | 230 | 21.1 ± 2.0 | 23.3 ± 2.3 | 22.1 ± 3.1 | 22.8 ± 5.8 | 23.1 ± 4.0 |
| Low-Dose Group | 20 | 85 | 20.6 ± 2.1 | 22.7 ± 2.4 | 23.1 ± 3.5 | 24.2 ± 3.7 | 24.3 ± 5.6 |
| Medium-Dose Group | 20 | 170 | 21.5 ± 1.9 | 23.4 ± 2.5 | 23.3 ± 2.6 | 24.5 ± 2.8 | 25.2 ± 3.2 |
| High-Dose Group | 20 | 510 | 22.0 ± 2.2 | 24.1 ± 2.2 | 23.4 ± 3.3 | 26.0 ± 3.9 | 26.2 ± 4.8 |

| Group | 20 d | 27 d | 34 d | 41 d | 48 d | 55 d |
|---|---|---|---|---|---|---|
| Blank Group | 40.8 ± 1.8 | 42.6 ± 2.4 | 44.7 ± 2.7 | 45.7 ± 3.3 | 46.7 ± 4.4 | 46.3 ± 5.2 |
| Negative control group | 39.0 ± 2.9 | 39.1 ± 3.6 | 40.1 ± 3.3 | 41.2 ± 3.4 | 42.5 ± 4.0 | 39.5 ± 4.1** |
| Model Group | 24.6 ± 4.1## | 27.2 ± 4.7# | 29.9 ± 4.8# | 29.5 ± 5.1# | 22.4 ± 3.7## | 25.8 ± 4.2### |
| Positive control group | 25.6 ± 5.4 | 25.3 ± 4.2 | 27.8 ± 4.1 | 29.1 ± 4.8 | 27.0 ± 5.4 | 27.2 ± 5.2 |
| Low-Dose Group | 28.6 ± 5.4 | 30.4 ± 5.3 | 32.2 ± 5.0 | 34.4 ± 5.9 | 35.6 ± 7.2** | 30.6 ± 6.4 |
| Medium-Dose Group | 26.1 ± 4.3 | 26.8 ± 5.5 | 29.4 ± 4.3 | 29.8 ± 3.4 | 33.7 ± 4.5** | 28.0 ± 3.8 |
| High-Dose Group | 25.3 ± 6.4 | 27.6 ± 7.0 | 32.3 ± 6.7 | 34.0 ± 7.0 | 30.3 ± 10.7* | 31.0 ± 9.5* |

Comment: comparing with the blank group, #P < 0.05, ##P < 0.01, ###P < 0.001; comparing with the model group, *P < 0.05, P < 0.01, *P < 0.001; and comparing with the positive control group, &P < 0.05, &&P < 0.01.

It can be concluded from the Table 1 that after alloxan modeling of the animals, body weights of the animals obviously decreased and showed representative characteristics of diabetes, i.e., three aspects were high and one aspect was low (eating a lot, drinking a lot, urinating a lot, while low weight). The test sample alleviated the decrease of the mouse weight, and increased body's resistance to adverse reaction. Especially in the later period of the experiments, the medium- and high-dose group showed significant differences. In addition, in the later period (the 55$^{th}$ day of administration), the body weight of the negative control group mice was controlled, wherein comparing with the weight of the mice in the blank group, there was no statistically significant difference, but the weight was obviously decreased.

4.3.2 Organ Coefficient

After administration of the test sample, the hearts, livers, spleens, lungs, kidneys and pancreases of the mice in each group were weighed respectively, and organ coefficients of each group were compared. The results were shown in Table 2.

TABLE 2

Organ coefficients of the mice

| Group | Number of Animals | Dosage (mg/kg) | Heart Coefficient | Liver Coefficient | Spleen Coefficient | Lung Coefficient | Kidney Coefficient | Pancreas Coefficient |
|---|---|---|---|---|---|---|---|---|
| Blank Group | 15 | — | 0.45 ± 0.08 | 4.16 ± 0.49 | 0.28 ± 0.05 | 0.49 ± 0.09 | 1.44 ± 0.30 | 0.58 ± 0.12 |
| Negative control group | 13 | 510 | 0.51 ± 0.10 | 4.61 ± 0.59 | 0.44 ± 0.18 | 0.56 ± 0.07 | 1.50 ± 0.12 | 0.59 ± 0.13 |
| Model Group | 12 | — | 0.47 ± 0.10 | 5.64 ± 0.34 | 0.29 ± 0.07 | 0.67 ± 0.09 | 2.26 ± 0.19 | 0.71 ± 0.19 |
| Positive control group | 11 | 230 | 0.50 ± 0.09 | 4.96 ± 1.67 | 0.47 ± 0.37* | 0.67 ± 0.14 | 2.17 ± 0.61 | 0.76 ± 0.31 |
| Low-Dose Group | 13 | 85 | 0.54 ± 0.07 | 5.71 ± 0.63 | 0.41 ± 0.12 | 0.70 ± 0.11 | 2.36 ± 0.32 | 0.63 ± 0.13 |
| Medium-Dose Group | 13 | 170 | 0.49 ± 0.09 | 5.92 ± 0.99 | 0.32 ± 0.08$^{\&}$ | 0.64 ± 0.21 | 2.44 ± 0.45 | 0.85 ± 0.29 |
| High-Dose Group | 10 | 510 | 0.55 ± 0.18 | 6.23 ± 1.54 | 0.38 ± 0.11 | 0.75 ± 0.19 | 2.51 ± 0.46 | 0.58 ± 0.20 |

Comment: comparing with the blank group, #P < 0.05, ##P < 0.01, ###P < 0.001; comparing with the model group, *P < 0.05, P < 0.01, *P < 0.001; and comparing with the positive control group, $^{\&}$P < 0.05, &&P < 0.01.

It can be concluded from Table 2 that the test sample in each group did not have obvious effects on organ coefficients of the mice, indicating that the test sample was relative safe.

4.3.3 Fasting Blood Glucose Value, Area Under the Blood Glucose Curve and Blood Glucose Decreasing Rate between the negative control group and the blank group, indicating that the drug has no effect on blood glucose of normal animals. There were significant differences between the positive control group and the model group, indicating that metformin significantly improved symptom of the hyperglycemia. In the first 30 days, there was no significant difference between the high-, medium-, and low-dose group of the test sample and the model group, indicating that the test sample had no significant effect on lowering blood glucose level. However, when extending to the 45$^{th}$ day, the high-dose group showed a significant effect on lowering blood glucose level (P<0.05). Continuously administrating to the 55$^{th}$ day, the fasting blood glucose level was tested again, and the results showed that the high-dose group has a significant effect on lowering blood glucose level and the effect was better than that of the positive control group (P<0.05).

TABLE 3

Blood glucose of the mice (mmol/L)

| Group | Number of Animals | Dosage (mg/kg) | 0 d | 16 d | 30 d | 45 d | 55 d |
|---|---|---|---|---|---|---|---|
| Blank Group | 15 | — | 6.29 ± 1.36 | 5.14 ± 1.27 | 6.66 ± 2.93 | 7.54 ± 2.73 | 6.04 ± 1.51 |
| Negative control group | 18 | 510 | 6.18 ± 0.88 | 4.95 ± 0.72 | 6.09 ± 1.76 | 5.83 ± 1.97 | 4.72 ± 1.28 |
| Model Group | 18 | — | 23.18 ± 3.93### | 22.61 ± 5.75### | 24.84 ± 5.00### | 27.15 ± 6.03### | 25.13 ± 9.66### |
| Positive control group | 20 | 230 | 22.87 ± 3.66 | 13.60 ± 4.82** | 15.57 ± 5.85* | 18.28 ± 5.86** | 17.93 ± 10.23 |
| Low-Dose Group | 20 | 85 | 22.79 ± 4.16 | 25.54 ± 5.40 | 27.69 ± 5.60 | 26.79 ± 7.75 | 20.16 ± 10.05 |
| Medium-Dose Group | 20 | 170 | 23.29 ± 3.86 | 20.56 ± 6.70 | 27.93 ± 3.36 | 26.40 ± 7.80 | 19.91 ± 9.47 |
| High-Dose Group | 20 | 510 | 22.92 ± 4.37 | 19.85 ± 7.22 | 24.00 ± 7.15 | 20.64 ± 7.01* | 14.37 ± 9.82*$^{\&}$ |

Comment: comparing with the blank group, #P < 0.05, ##P < 0.01, ###P < 0.001; comparing with the model group, *P < 0.05, P < 0.01, *P < 0.001; and comparing with the positive control group $^{\&}$P < 0.05, &&P < 0.01.

Comment: the low dose was equal to 5 times of the human recommended amount, the medium dose was equal to 10 times of the human recommended amount and the high dose was equal to 30 times of the human recommended amount.

As shown in Table 3, comparison of the blank group and the model group indicated that the modeling was successful. There was no significant change in the blood glucose level

TABLE 4

Area under the blood glucose curve of the mice (mmol/L)

| Group | Number of Animals | Dosage (mg/kg) | 45 d | 55 d |
|---|---|---|---|---|
| Blank Group | 15 | — | 19.40 ± 4.84 | 15.08 ± 3.08 |
| Negative control group | 18 | 510 | 15.25 ± 6.62 | 14.09 ± 4.50 |

TABLE 4-continued

Area under the blood glucose curve of the mice (mmol/L)

| Group | Number of Animals | Dosage (mg/kg) | 45 d | 55 d |
|---|---|---|---|---|
| Model Group | 18 | — | 55.23 ± 4.91### | 57.35 ± 10.65### |
| Positive control group | 20 | 230 | 48.30 ± 11.46* | 44.45 ± 16.41* |
| Low-Dose Group | 20 | 85 | 60.62 ± 9.94 | 46.66 ± 16.83 |
| Medium-Dose Group | 20 | 170 | 60.01 ± 5.99 | 47.86 ± 16.36 |
| High-Dose Group | 20 | 510 | 54.37 ± 10.40 | 33.29 ± 18.12**& |

Comment:

comparing with the blank group, #P < 0.05, ##P < 0.01, ###P < 0.001; comparing with the model group, *P < 0.05, P < 0.01, *P < 0.001; and comparing with the positive control group, &P < 0.05, &&P < 0.01.

It can be concluded from the Table 4 that the high-dose group obviously improved the area under the blood glucose curve of the alloxan-induced mice (P<0.01), and the effect of which was even better than that of the positive drug metformin.

TABLE 5

Blood glucose decreasing rate of the mice

| Group | Number of animals | Dosage (mg/Kg) | 45 d | 55 d |
|---|---|---|---|---|
| Blank Group | 15 | — | −19.76% ± 0.60 | 4.07% ± 0.30 |
| Model Group | 18 | — | −17.14% ± 0.41 | −8.40% ± 0.51 |
| Positive control group | 20 | 230 | −20.06% ± 0.30* | 21.60% ± 0.48 |
| Low-Dose Group | 20 | 85 | −17.56% ± 0.42 | 11.51% ± 0.42 |
| Medium-Dose Group | 20 | 170 | −13.35% ± 0.43 | 14.52% ± 0.45 |
| High-Dose Group | 20 | 510 | 9.96% ± 0.46 | 37.30% ± 0.49 |
| Negative control group | 18 | 510 | 5.72% ± 0.48 | 23.71% ± 0.31 |

Comment:

comparing with the blank group, #P < 0.05, ##P < 0.01, ###P < 0.001; and comparing with the model group, *P < 0.05, **P < 0.01.

As shown in Table 5, on the $55^{th}$ day, the high-dose group significantly lowered the blood glucose level of the diabetic mice, and the administration effect in long term was better than that of the metformin.

4.4 Experimental Results:

From the researches above we found that the powder formulation prepared in the Example 3 has no effect on blood glucose of normal mice, but can control the body weight of the mice and improve quality of their lives (mainly performed in aspects such as hair color, liveness and so on). In addition, high-dose administration in the long term improved the blood glucose level of the mice. Although it did not reach drug efficacy, it met the evaluation standard of hypoglycemic of health care food.

The powder formulations obtained in Example 1 and Example 2 have a similar effect as that of Example 3.

5. Effects of the Test Sample on Blood Glucose Level of Diabetic Rats 5.1 Grouping and Administration Duration of the Test Sample In the experiment, there were three dosing groups of the test sample, one model group, one positive control group (metformin hydrochloride tablets) and one blank group. The method for preparing the three test sample groups were shown hereinafter.

Method for preparing the solution of the test sample (500 mg/kg): 2.3011 g of the test sample was precisely weighed and 46 mL of distilled water was added to prepare a solution of 0.05 g/mL, i.e., high-dose group of the test sample (500 mg/kg, 1 mL/100 g), which was equal to 30 times the recommended amount for human.

Method for preparing the solution of the test sample (170 mg/kg): 0.6970 g of the test sample was precisely weighed and 41 mL of distilled water was added to prepare a solution of 0.017 g/mL, i.e., medium-dose group of the test sample (170 mg/kg, 1 mL/100 g), which was equal to 10 times the recommended amount for human.

Method for preparing the solution of the test sample (85 mg/kg): 0.3396 g of the test sample was precisely weighed and 40 mL of distilled water was added to prepare a solution of 0.0085 g/mL, i.e., low-dose group of the test sample (85 mg/kg, 1 mL/100 g), which was equal to 5 times the recommended amount for human.

Method for preparing the positive control sample: the metformin hydrochloride tablet was milled into fine powders by a mortar, 0.9329 g powder was precisely weighed and transferred to a 100 mL-beaker. 43 mL of distilled water was added by using a 100 mL-graduated cylinder, preparing solution with a concentration of 0.017 g/mL, i.e., metformin positive control group for rat (170 mg/kg, 1 ml/100 g), which was equal to 10 times the recommended amount for human.

The rats were weighed after 1-day adaptive feed, and the rats were weighed once a week and recorded.

5.2 Test of Fasting Blood Glucose and Glucose Tolerance in Rat

After 5-day of adaptive housing with normal feeding, the rats were fasted for 3 to 4 hours and blood samples were taken from the tails. The fasting blood glucose value, which was the blood glucose value before administration of glucose (0 hour), was tested. After administration of 2.5 g/kgBW glucose, the blood glucose level was tested at the 0.5 hour and the $2^{nd}$ hour as the basal value of that batch of animals. The rats were divided into 6 groups according to the blood glucose value at 0 hour and the 0.5 hour, including one blank group, one positive control group, one model group and 3 dosing groups of the test sample. There were 20 rats in the high-dose group, and 18 rats in the other groups. The blank group was not treated. The positive control group was administered with metformin solution by intragastric gavage. The 3 dosing groups of the test sample were administered with test sample solutions of different concentrations by intragastric gavage. The model group was administered with the solvent of the same volume. The administration lasted for 45 days. Normal feeds were provided to all groups. One week later, high calorie feeds were provided to the model group, positive control group and three dosing groups of the test sample. 30 days after the feeding, the rats were fasted for 24 hours. The model group and the three dosing groups of the test sample were respectively peritoneal injected with alloxan of 200 mg/kgBW (the injection amount was 1 mg/100 g weight) on the base of high calorie feed. The model group and 3 dosing groups of the test sample were continuously fed on high calorie feeds for 3 days. When the experiment ended, animals in each group were fasted for 3 to 4 hours, and the fasting blood glucose, glucose tolerance and area under the blood glucose curve were measured.

$$\text{Area under the blood glucose curve} = \frac{(\text{Blood glucose at 0 hour} + \text{Blood glucose at the 0.5th hour}) \times 0.5}{2} + \frac{(\text{Blood glucose at the 2nd hour} + \text{Blood glucose at the 0.5th hour}) \times 1.5}{2}$$

5.2 Test of Cholesterol Level and Triglyceride Level

After the experiment, the rats in each group were fasted for 3 to 4 hours and peritoneal injected with pentobarbital sodium solution (1 mL/100 g) for anesthesia. 8 mL of blood was taken from the femoral artery and centrifuged at 4500 r for 6 minutes at 4° C. The serum was taken and the cholesterol level was tested by a cholesterol kit, and the triglyceride level was tested by a triglyceride kit.

5.3 Organ Coefficient

The rats were subjected to euthanasia and dissection. Hearts, livers, spleens, lungs, kidneys and parts of the pancreases of the rats were weighed, imaged and recorded, respectively. The organ coefficients were calculated. In addition, pancreases from each group were respectively immersed into formalin-containing bottles.

5.4 Experimental Results and Discussion 5.4.1 Graph of Body Weight Growth

The Table 6 showed that body weight of the diabetic rats rose obviously in the medium period of the experiment, which was much more than the weight of the normal rats. However, in the later period, there was an obvious reduction, which was in line with the typical characteristics of type II diabetes.

TABLE 6

Weight changes of rats

| Group | Number of Animals | Dosage (mg/kg) | 3 d | 6 d | 8 d | 12 d |
|---|---|---|---|---|---|---|
| Blank Group | 18 | — | 206.44 ± 10.91 | 225.78 ± 12.01 | 239.11 ± 10.93 | 268.44 ± 8.25 |
| Model Group | 18 | — | 205.22 ± 11.02 | 227.33 ± 12.95 | 243.94 ± 14.74 | 280.50 ± 20.03[#] |
| Positive control group | 18 | 170 | 207.00 ± 10.91 | 225.22 ± 12.01 | 244.28 ± 10.93 | 277.50 ± 8.25 |
| Low-Dose Group | 18 | 85 | 207.11 ± 13.82 | 228.39 ± 13.97 | 248.17 ± 15.32 | 278.94 ± 20.23 |
| Medium-Dose Group | 18 | 170 | 208.11 ± 9.99 | 227.83 ± 9.47 | 246.06 ± 10.38 | 278.61 ± 14.67 |
| High-Dose Group | 20 | 500 | 211.50 ± 13.26 | 233.15 ± 14.02 | 251.75 ± 14.11 | 288.25 ± 16.16 |

| Group | 22 d | 28 d | 35 d | 42 d | 45 d |
|---|---|---|---|---|---|
| Blank Group | 291.50 ± 18.39 | 334.00 ± 21.40 | 349.89 ± 23.32 | 366.39 ± 21.22 | 376.29 ± 27.43 |
| Model Group | 346.83 ± 27.34[###] | 393.39 ± 36.62[###] | 418.83 ± 40.60[###] | 412.72 ± 43.48[###] | 334.94 ± 35.99[###] |
| Positive control group | 325.89 ± 18.39* | 373.67 ± 21.40 | 396.22 ± 23.32* | 403.83 ± 21.22 | 361.19 ± 27.43 |
| Low-Dose Group | 340.67 ± 35.64 | 385.76 ± 32.53 | 418.28 ± 38.51 | 440.06 ± 41.18 | 355.59 ± 39.42 |
| Medium-Dose Group | 339.83 ± 39.71 | 373.89 ± 26.35 | 413.50 ± 38.11 | 430.94 ± 42.38 | 348.14 ± 39.99 |
| High-Dose Group | 352.90 ± 21.81 | 387.80 ± 36.00 | 418.95 ± 32.80 | 422.60 ± 35.70 | 356.68 ± 37.51 |

Comment: comparing with the blank group, [#]$P < 0.05$, [##]$P < 0.01$, [###]$P < 0.001$; and comparing with the model group, *$P < 0.05$, **$P < 0.01$.

5.4.2 Organ Coefficient

TABLE 7

Organ coefficient of rats

| Group | Number of Animals | Dosage (mg/kg) | Heart Coefficient | Liver Coefficient | Spleen Coefficient | Lung Coefficient | Kidney Coefficient | Pancreas Coefficient |
|---|---|---|---|---|---|---|---|---|
| Blank Group | 18 | — | 0.35 ± 0.05 | 3.48 ± 0.45 | 0.27 ± 0.15 | 0.50 ± 0.05 | 0.75 ± 0.13 | 0.31 ± 0.11 |
| Model Group | 18 | — | 0.37 ± 0.06 | 3.21 ± 0.51## | 0.10 ± 0.03### | 0.56 ± 0.12 | 0.87 ± 0.12# | 0.42 ± 0.25 |
| Positive control group | 18 | 170 | 0.36 ± 0.06 | 3.36 ± 0.48 | 0.16 ± 0.09* | 0.53 ± 0.15 | 0.88 ± 0.20 | 0.37 ± 0.13 |
| Low-Dose Group | 18 | 85 | 0.37 ± 0.05 | 3.44 ± 0.37 | 0.14 ± 0.08 | 0.56 ± 0.15 | 0.93 ± 0.17 | 0.38 ± 0.15 |
| Medium-Dose Group | 18 | 170 | 0.36 ± 0.05 | 3.45 ± 0.52 | 0.11 ± 0.04 | 0.58 ± 0.14 | 0.90 ± 0.06 | 0.44 ± 0.25 |
| High-Dose Group | 20 | 500 | 0.37 ± 0.06 | 3.57 ± 0.93 | 0.12 ± 0.07 | 0.58 ± 0.21 | 0.89 ± 0.12 | 0.35 ± 0.14 |

Comment: comparing with the blank group, #P < 0.05, ##P < 0.01, ###P < 0.001; and comparing with the model group, *P < 0.05, **P < 0.01.

TABLE 8

Blood glucose value of rats in different periods

| Group | Number of Animals | Dosage (mg/kg) | 4D | | | 45D | | |
|---|---|---|---|---|---|---|---|---|
| | | | Blood Glucose at 0 hour | Blood Glucose at 0.5 hour | Blood Glucose at $2^{th}$ hour | Blood Glucose at 0 hour | Blood Glucose at 0.5 hour | Blood Glucose at $2^{th}$ hour |
| Blank Group | 18 | — | 6.10 ± 1.18 | 8.17 ± 1.79 | 5.71 ± 0.74 | 4.44 ± 1.13 | 6.07 ± 1.25 | 4.59 ± 0.65 |
| Model Group | 18 | — | 5.95 ± 1.26 | 8.22 ± 1.25 | 5.79 ± 1.26 | 19.66 ± 5.11### | 19.56 ± 5.69### | 21.53 ± 5.90### |
| Positive control group | 18 | 170 | 6.00 ± 0.87 | 8.33 ± 1.54 | 5.75 ± 0.97 | 12.05 ± 4.98*** | 15.98 ± 4.87 | 13.31 ± 5.83*** |
| Low-Dose Group | 18 | 85 | 6.03 ± 0.72 | 8.17 ± 1.00 | 5.92 ± 1.24 | 16.09 ± 6.46 | 17.81 ± 5.95 | 20.20 ± 6.25 |
| Medium-Dose Group | 18 | 170 | 6.03 ± 0.74 | 8.08 ± 1.23 | 5.46 ± 0.76 | 14.84 ± 6.52* | 16.67 ± 6.70 | 18.31 ± 6.80 |
| High-Dose Group | 20 | 500 | 6.09 ± 0.86 | 8.02 ± 1.41 | 5.71 ± 1.01 | 14.04 ± 5.86** | 16.18 ± 6.11 | 16.06 ± 5.12** |

Comment: comparing with the blank group, #P < 0.05, ##P < 0.01, ###P < 0.001; and comparing with the model group, *P < 0.05, **P < 0.01.

Comment: the low dose was equal to 5 times of the human recommended amount, the medium dose was equal to 10 times the recommended amount for human and the high dose was equal to 30 times the recommended amount for human.

As shown in Table 8, the blank group showed significant difference (P<0.001) compared with the model group, indicating that the modeling was successful. The fasting blood glucose results demonstrated: there were significant differences between the positive control group and the model group, indicating that metformin significantly improved symptom of the hyperglycemia; after 45-day administration of the test sample, there were significant differences between the medium-dose and high-dose groups and the model group, indicating that the test sample has relatively obvious effect on lowering the blood glucose level (P<0.05, P<0.01), and presented a certain dose-dependent effect.

TABLE 9

Area under the blood glucose curve of rats (mmol/L)

| Group | Number of Animals | Dosage (mg/kg) | 4 d | 45 d |
|---|---|---|---|---|
| Blank Group | 18 | — | 13.98 ± 2.12 | 10.62 ± 1.39 |
| Model Group | 18 | — | 14.05 ± 1.90 | 39.13 ± 9.66### |
| Positive control group | 18 | 170 | 14.15 ± 1.65 | 28.98 ± 9.74** |
| Low-Dose Group | 18 | 85 | 14.12 ± 1.55 | 36.98 ± 11.62 |
| Medium-Dose Group | 18 | 170 | 13.65 ± 1.43 | 34.12 ± 13.04 |
| High-Dose Group | 20 | 500 | 13.82 ± 1.60 | 31.74 ± 10.70 |

Comment:
comparing with the blank group, #$P < 0.05$, ##$P < 0.01$, ###$P < 0.001$; comparing with the model group, *$P < 0.05$, **$P < 0.01$.

It can be concluded from Table 9 that in the glucose tolerance test, area under the blood glucose curve at the $2^{nd}$ hour of the positive drug metformin showed significant differences, while the test sample groups did not show statistically significant difference. However, among the test sample groups, there was a certain dose-dependent effect.

5.4.3 Cholesterol Level and Triglyceride Level in Serum

The results were shown in Table 10.

TABLE 10

Triglyceride index and cholesterol index in serum of rats

| Group | Number of Animals | Dosage (mg/kg) | Triglyceride Index | Cholesterol Index |
|---|---|---|---|---|
| Blank Group | 17 | — | 0.43 ± 0.2 | 2.49 ± 0.85 |
| Model Group | 10 | — | 18.30 ± 6.81### | 10.05 ± 4.63### |
| Positive control group | 12 | 170 | 9.47 ± 5.29*** | 3.71 ± 1.57*** |
| Low-Dose Group | 7 | 85 | 14.22 ± 3.47* | 9.88 ± 2.02 |
| Medium-Dose Group | 7 | 170 | 9.29 ± 8.83** | 6.43 ± 2.33* |
| High-Dose Group | 12 | 500 | 13.42 ± 6.45* | 6.89 ± 4.47 |

Comment:
comparing with the blank group, #$P < 0.05$, ##$P < 0.01$, ###$P < 0.001$; comparing with the model group, *$P < 0.05$, **$P < 0.01$.

It can be concluded from Table 10 that after long-time high-fat high-carbohydrate feeding, the rats presented symptoms of hyperglycemia and hyperlipidemia. When comparing with the blank group, the levels of triglyceride and cholesterol in serum of the model group increased significantly ($P<0.001$). All the groups administered with test sample have relatively good effect on lowering blood lipid level; especially for triglycerides, all the groups showed statistically significant differences, and the medium-dose group has the best drug efficacy.

5.5 Results

Under the conditions of the present experiments, long-term administration of the powder formulation prepared in Example 3 decreased the blood glucose level and blood lipid level in insulin resistance rats, and these effects were similar to that of the positive drug metformin hydrochloride, thus indicating that the powder formulation has relatively good hypoglycemic and hypolipidemic functions, and it was adapt to be used for health care food.

The powder formulations obtained in Example 1 and Example 2 have similar effects as that of Example 3.

What is claimed is:

1. A method of lowering blood glucose level and blood lipid level, comprising administering a powder formulation to a subject in need thereof, wherein the powder formulation is made from starting materials consisting of inulin, FOLIUM CYCLOCARYA PALIURUS, RHIZOMA DIOSCOREA OPPOSITE, RADIX ASTRAGALUS MEMBRANACEUS, CAULIS DENDROBIUM and RADIX ET RHIZOMA SALVIA MILTIORRHIZA as starting materials, and the mass ratio of inulin, FOLIUM CYCLOCARYA PALIURUS, RHIZOMA DIOSCOREA OPPOSITE, RADIX ASTRAGALUS MEMBRANACEUS, CAULIS DENDROBIUM and RADIX ET RHIZOMA SALVIA MILTIORRHIZA is (0.5~3):(4~8):(0.5~3):(0.5~3):(0.1~2):(0.1~2).

2. The method according to claim 1, wherein the mass ratio of inulin, FOLIUM CYCLOCARYA PALIURUS, RHIZOMA DIOSCOREA OPPOSITE, RADIX ASTRAGALUS MEMBRANACEUS, CAULIS DENDROBIUM and RADIX ET RHIZOMA SALVIA MILTIORRHIZA is 1.5:8:1:1:0.4:0.1.

3. The method according to claim 1, wherein the mass ratio of inulin, FOLIUM CYCLOCARYA PALIURUS, RHIZOMA DIOSCOREA OPPOSITE, RADIX ASTRAGALUS MEMBRANACEUS, CAULIS DENDROBIUM and RADIX ET RHIZOMA SALVIA MILTIORRHIZA is 0.5:4:2:2:1:0.5.

4. The method according to claim 1, wherein the mass ratio of inulin, FOLIUM CYCLOCARYA PALIURUS, RHIZOMA DIOSCOREA OPPOSITE, RADIX ASTRAGALUS MEMBRANACEUS, CAULIS DENDROBIUM and RADIX ET RHIZOMA SALVIA MILTIORRHIZA is 1.2:6:1:1:0.5:0.5.

5. The method according to claim 1, wherein the powder formulation is in the form of a health food.

* * * * *